United States Patent [19]
Agar

[11] Patent Number: 5,101,163
[45] Date of Patent: Mar. 31, 1992

[54] OIL/WATER MEASUREMENT

[75] Inventor: Joram Agar, Grand Cayman,

[73] Assignee: Agar Corporation Ltd., Grand Cayman,

[21] Appl. No.: 675,061

[22] Filed: Mar. 26, 1991

Related U.S. Application Data

[63] Continuation of Ser. No. 417,658, Oct. 4, 1989, abandoned.

[51] Int. Cl.⁵ .................................... G01N 22/04
[52] U.S. Cl. .................................... 324/639; 324/640; 324/647; 324/698
[58] Field of Search ............... 324/637, 639, 640, 642, 324/643, 647, 641, 698; 73/61.1 R

[56] References Cited

U.S. PATENT DOCUMENTS

| | | | |
|---|---|---|---|
| 3,265,873 | 8/1966 | Sawyer | 324/639 X |
| 3,498,112 | 3/1970 | Howard | 73/61.1 |
| 3,551,806 | 12/1970 | Sasaki | 324/640 |
| 4,052,666 | 10/1977 | Fletcher et al. | 324/643 |
| 4,131,845 | 12/1978 | Pakulis | 324/640 |
| 4,257,708 | 3/1981 | Fukuda | 356/435 |
| 4,423,623 | 1/1984 | Ho et al. | 73/61 R |
| 4,486,714 | 12/1984 | Davis, Jr. et al. | 324/639 X |
| 4,499,418 | 2/1985 | Helms et al. | |
| 4,503,383 | 3/1985 | Agar et al. | 324/61 P |
| 4,634,963 | 1/1987 | Lunden | 324/639 X |
| 4,660,414 | 4/1987 | Hatton et al. | 73/61.1 R |
| 4,760,742 | 8/1988 | Hatton | 73/861.04 |
| 4,764,718 | 8/1988 | Revus et al. | 324/637 X |
| 4,774,680 | 9/1988 | Agar | 364/550 |
| 4,902,961 | 2/1990 | De et al. | 324/640 |

OTHER PUBLICATIONS

Patent Abstracts of Japan, vol. 2, No. 20, p. 11346E77, 2/9/78 & JP A, 52139464 (Tokyo Shibaura Denki) 11/21/77 (see abstract).

Review of Scientific Instruments, vol. 50, No. 10, 10/79, American Institute of Physics (US) N. Abuaf et al.: Radio-Frequency Probe for Bubble Size and Velocity Measurements, pp. 1260-1262, see paragraphs 1, 2.

Primary Examiner—Kenneth A. Wieder
Attorney, Agent, or Firm—Oblon, Spivak, McClelland, Maier & Neustadt

[57] ABSTRACT

A device for measuring the concentration of two substances through the transmission of electromagnetic waves. The device utilizes at least one transmission element for transmitting a signal and at least two receiving elements for receiving a signal from the at least one transmission element and providing first and second output signals. The present invention also utilizes a receiving device for receiving the first and second output signals from the at least two receiving elements such that the difference or ratio of the two signals is utilized to determine the concentration.

15 Claims, 5 Drawing Sheets

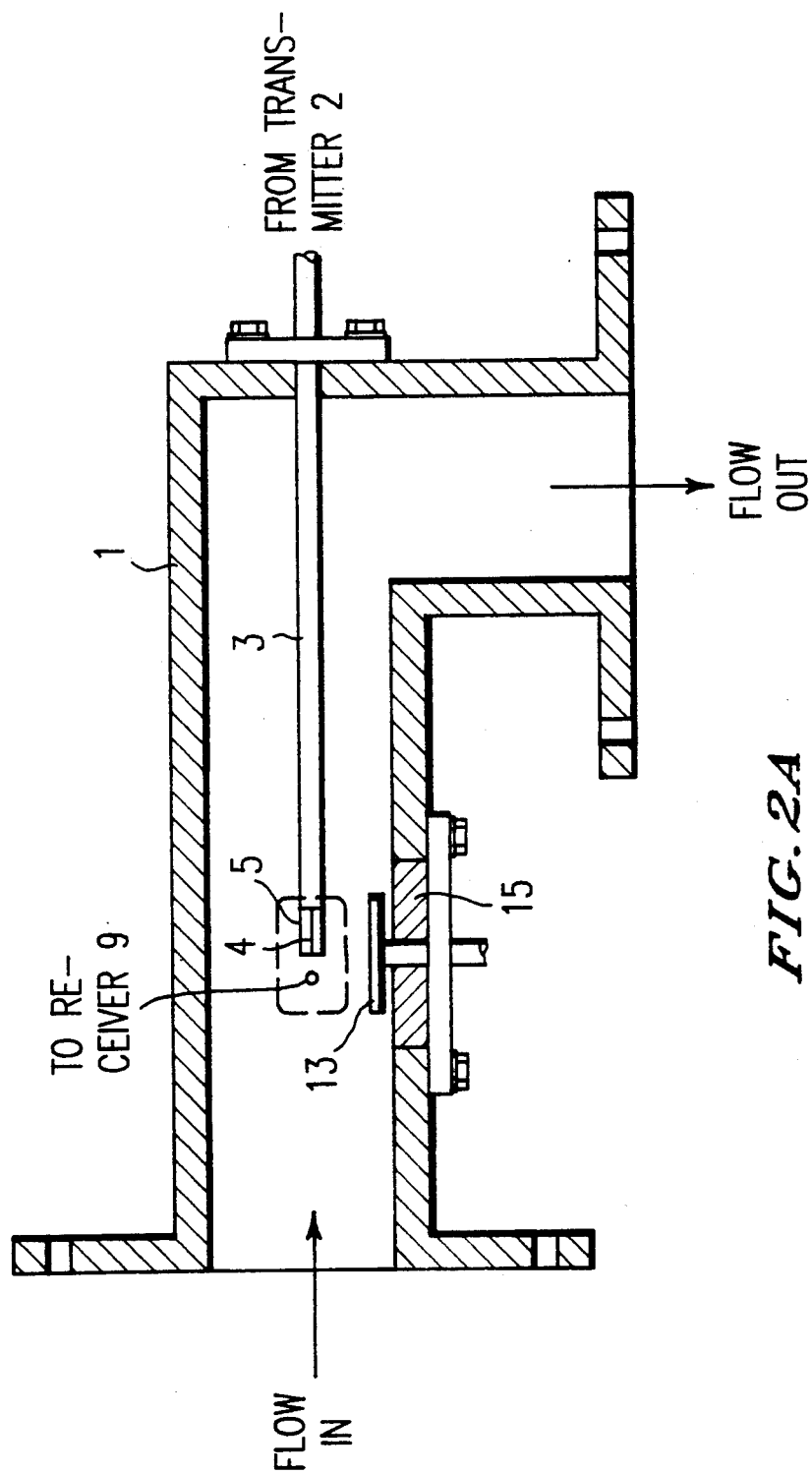

OIL/WATER MEASUREMENT

This application is a continuation of application Ser. No. 07/417,658, filed on Oct. 4, 1989, now abandoned.

BACKGROUND OF THE INVENTION

1. Field of the Invention

The present invention relates to a device to measure content and velocity of aqueous and hydrocarbon mixtures in both oil-continuous and water-continuous phases.

2. Description of the Related Art

There are numerous devices on the market which utilize the change in the dielectric constant to determine the amount of water in oil. These devices operate only in the oil-continuous phase, i.e. as long as the mixture behaves like a dielectric. However, as soon as the mixture changes to water-continuous, it stops being an insulator (dielectric) and the instrument indicates 100% water.

Other techniques which utilize optical principles suffer from a lack of sensitivity at the oil-continuous phase and cannot cope with thick oil build-up without frequent cleaning. Changes in the salinity of the water also tend to affect the absolute measurement of such parameters, e.g. refractive index, conductivity, dielectric constant, etc. Nuclear absorption, while giving good results with binary mixtures, are overmasked by heavy metallic contaminants, such as sulfur, vanadium, etc. Particle size in the water-continuous phase also plays an important part and affects the reading greatly.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 2A shows another embodiment of the present invention using a "patch" type antenna;

DESCRIPTION OF THE PREFERRED EMBODIMENTS

Figure 1:
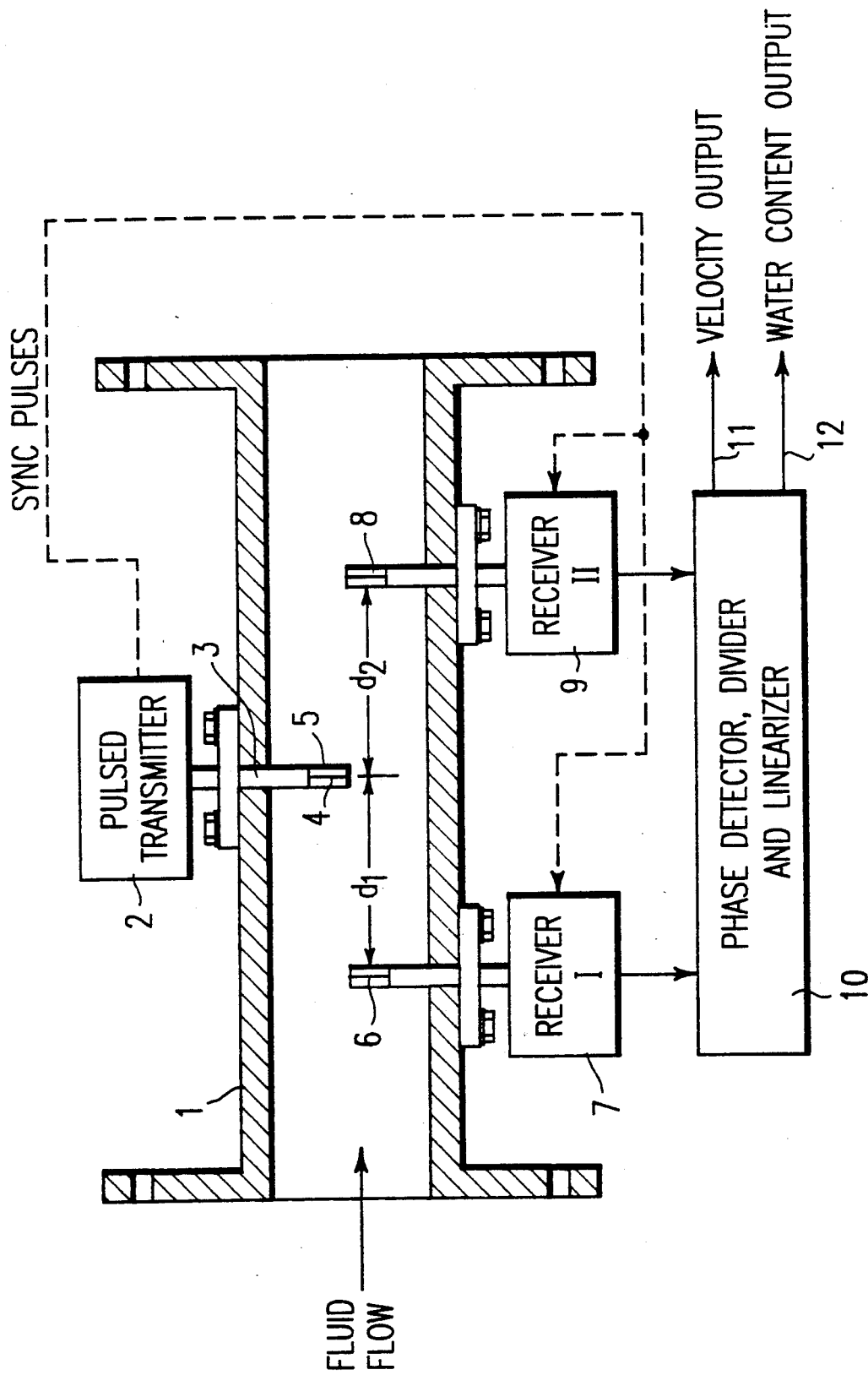
FIG. 1 show the conduit and measuring system of the present invention.

FIG. 1 describes such system which carries the dual purpose of measuring the hydrocarbon/water ratio and fluid velocity.

FIG. 1 shows a conduit (1) for the fluid flow. the conduit (1) may have a circular or rectangular cross-section. Transmitter (2) transmits a high frequency signal via a coaxial cable (3) or a wave guide to an antenna (4) which can be any known antenna suitable in relation to the frequency of the high frequency signal transmitted by the transmitter (2), which is insulated from the fluid by means of an insulator (5). Receivers (7) and (9) are connected to similar antennae arrangements (6) and (8), which are spaced from the transmitting antenna (4) distance "$d_1$" and "$d_2$" where "$d_2$" is normally twice "$d_1$". A divider (10) divides the outputs of receivers (7) and (9) and supplies a linearized output of the ratio of $P_1/P_2$, wherein $P_1$ is the value of the signal received at (7) and $P_2$ is the value of the signal received at (9). Accordingly, either a vector ratio, a vector difference or the phase difference between the two receiving signals can be used to measure the concentration of the two substances to be measured. This linearizer may take the form of the curve selector linearizer, as disclosed in U.S. Pat. No. 4,774,680.

The "electrical loading" or impedance of fluid acting on antenna (4) will vary with the electrical characteristics of the fluid (this phenomena was utilized in U.S. Pat. No. 4,503,383) and thus the amount of energy transmitted will be affected by the nature of the fluid. The major problem with devices that utilize such measuring techniques is that the fluid and the surface of insulator (5) predominates the effect, in particular when the fluid consists of two immicible fluids such as water with a few drops of oil in it. If this mixture is not homogeneous, or the droplets size and coated thickness vary, the loading will be greatly affected by it. U.S. Patent application Ser. No. 07/311,610 is trying to overcome it by trying to predict this effect and prediction requires many tests to get the required parameters, and is only correct for a restricted range of products, temperature and velocity. Thus, if one can measure the bulk properties of this fluid, these problems are overcomed.

The present invention achieves these goals by measuring the ratio and/or the phase difference of the powers received by each receiver (7) and (9). As oil absorbs very little energy while water does, the amount of power received in each antenna is a function of the water content and the distance from the transmitting antenna. B taking the ratio and/or the phase difference of these signals, output (12) becomes independent of surface coating, etc. as both antennae (6) and (8) are exposed to the same fluid in exactly the same way. By installing the antennae axially with the flow, and in such a way that one receiving antenna receives its signal with the direction of the flow, while the other, which is equally spaced, receives its signal against the direction of flow, the phase difference between these two received signals is directly proportional to the flow's velocity.

By transmitting at a frequency where the phase difference between the two signals due to the dielectric constant of water $E=E'-jE''$ is maximum (around 2.45 GHz) the effect of salinity is greatly reduced. Also by using two or more distinct frequencies, say 2.45 GHz and 15 GHz, one can obtain more inside information about the fluids' components. Higher frequencies such as infrared, visual light, ultraviolet, X-rays and gamma-rays are also applicable. Naturally, the "antennae" will be made to suit each wavelength.

FIG. 2A shows another embodiment of the invention, according to which the receiving "monopole" antennae are replaced by two "patch" type (or similar) antennae.

All the other features such as the transmitter (2) and Phase Detector (10) of FIG. 1 are also common to FIG. 2A. The antennae arrangement in FIG. 2A is shown in 2 planes perpendicular to each other to demonstrate that two pairs of antennae can be used in any plane, not necessarily just opposite each other as shown in FIG. 1. Note that for clarity, only one pair is shown in FIG. 2A. The other pair is omitted for clarity sake. Also, only the "Patch" type is shown. Naturally, other types of known antennae configurations can be used, such as "horn", monopoles, dipoles, etc.

Figure 2B:
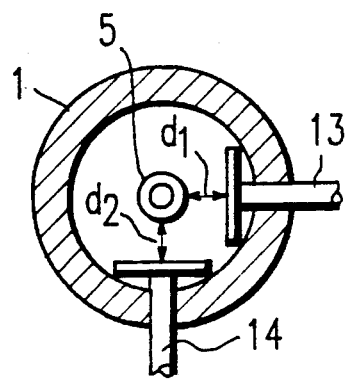
FIG. 2B show an end view of FIG. 2A.
Figure 2C:
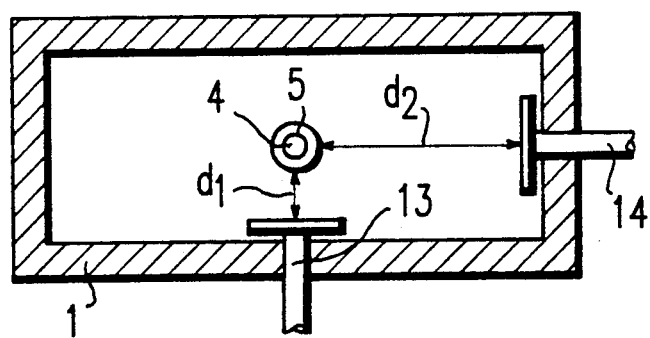
FIG. 2C shows a similar arrangement to FIG. 2B but having a rectangular cross-section.

FIG. 2B shows an end view of FIG. 2A, where one monopole transmitter antenna (4) is used in the center and two receiving antennae (13) and (14). FIG. 2B shows a circular cross-section waveguide, while FIG. 2C shows a similar arrangement with a rectangular cross-section waveguide. Again, other types of conventional antennae can be used in this configuration such as two pairs of monopoles, "horn" type, etc. The transmitting antenna can be shared, or split into two separate ones. The advantage of two separate pairs is the elimination of cross-coupling between one receiving antenna and the other. The peripheral equipment surrounding the prime sensor is the same as shown in FIG. 1.

Figure 3:
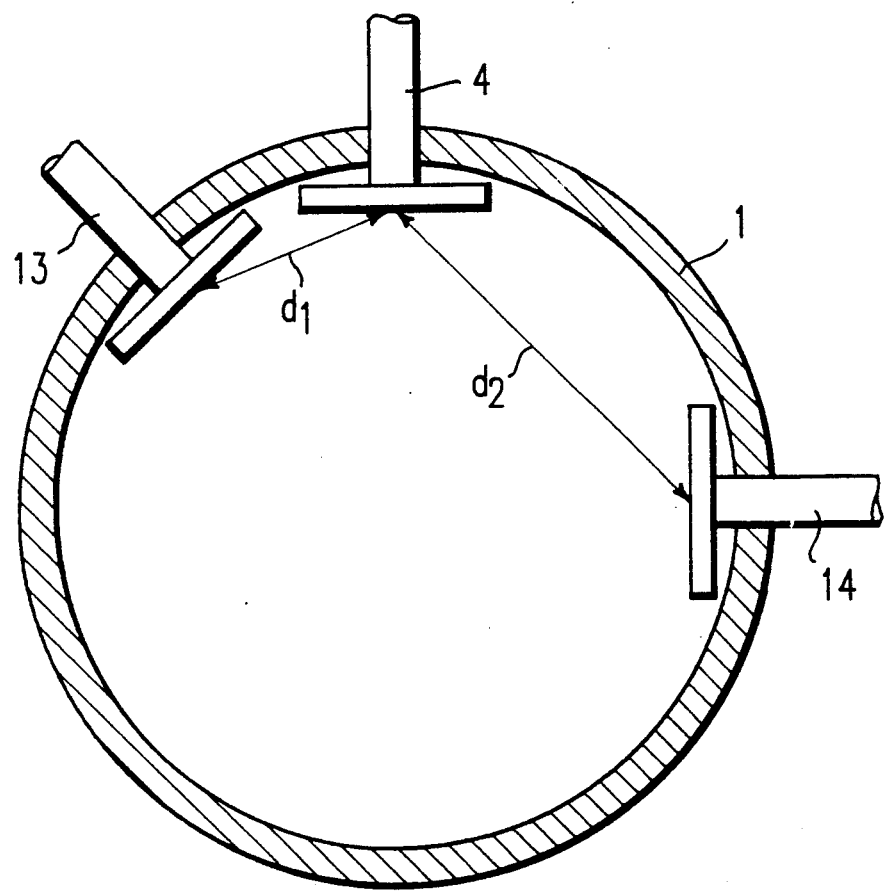
FIG. 3 shows another embodiment of the present invention.

FIG. 3 shows another possible way to achieve the same end, using one dipole transmitting antenna, and two dipole receiving antennae. The drawing shows such arrangement in a circular waveguide. Naturally, the more conventional rectangular waveguide can also be used. FIG. 3 shows how to achieve the required differential distances $d_1$ and $d_2$ in one specific way. The antennae can be located in one plane, or spaced axially, too. Spacing the antennae axially lowers their cross-coupling which improves the linearity of the measured signal. Again, instead of sharing one transmitter antenna, two independent pairs can be used to further reduce the cross-coupling. The peripheral equipment is the same as shown in FIG. 1.

Figure 4:
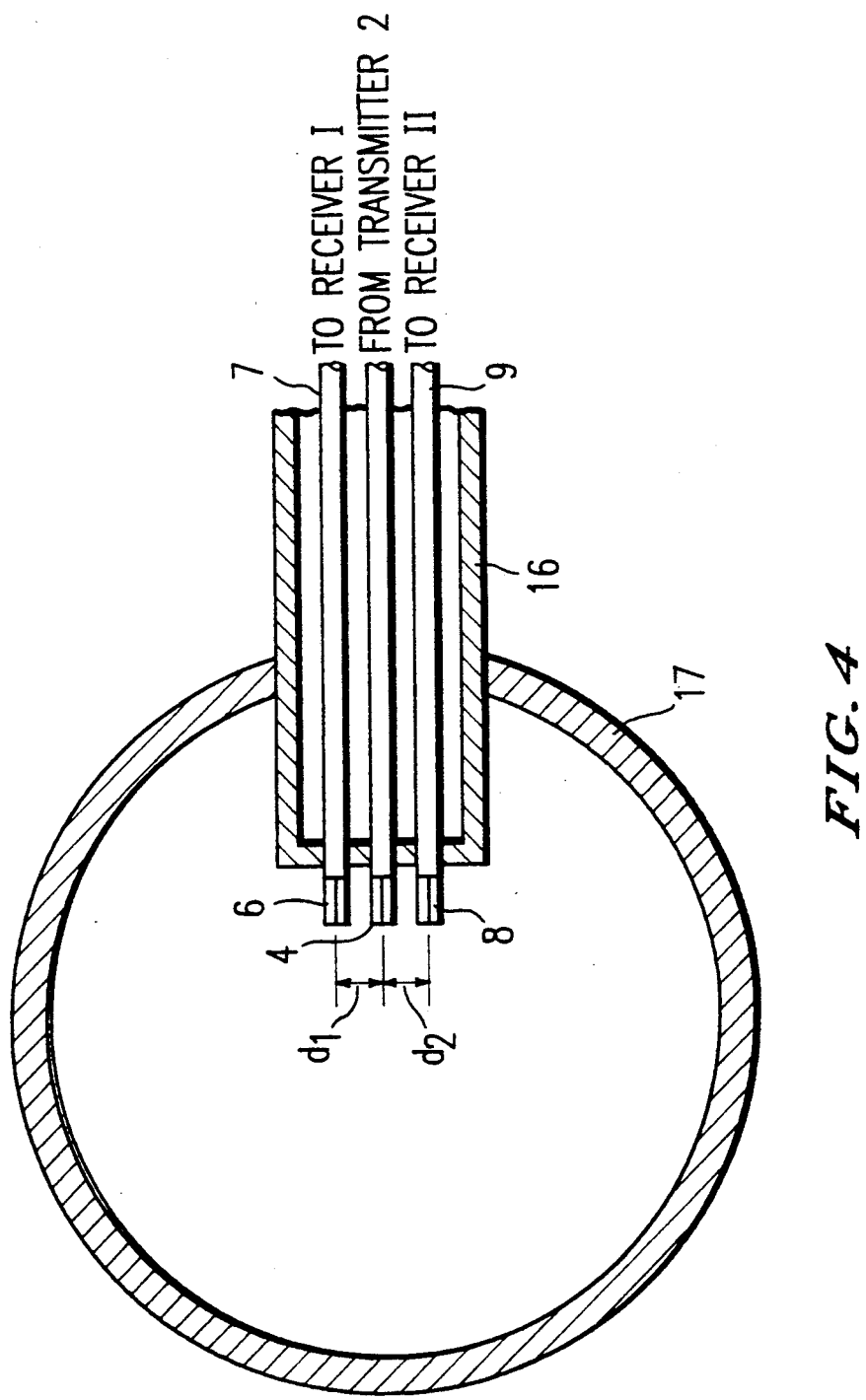
FIG. 4 shows another embodiment of the present invention using an insertion type probe.

FIG. 4 shows an insertion-type probe (16) inserted into a large conduit (17). Again, instead of the monopoles shown, dipoles and other type antennae can be used. Probe (16) is shown welded to pipe (17), but any other form of attachment can be used, e.g. the use of a seal-housing as described in U.S. Pat. No. 4,503,383. Similar peripheral electronics as described in FIG. 1 can be used for signal conversion.

What is claimed as new and desired to be secured by Letters Patent of the United States is:

1. A device for measuring the concentration of two substances by means of the transmission of electromagentic waves through a mixture of said two substances, said device comprising:
   a transmitter for transmitting through said mixture of said two substances a signal within a predetermined frequency band;
   first and second receiving elements for receiving the signal transmitted by said transmitter through said mixture of said two substances and providing respective first and second output signals, said receiving elements being placed at two different distances from said transmitter; and,
   means for processing the first and second output signals to determine the concentration of the two substances using only the first and second output signals as variables obtained by means of transmission and reception of signals through said mixture of said two substances.

2. A device according to claim 1, wherein said processing means comprises:
   means for determining the ratio of the powers of the received first and second output signals;
   means for determining a phase difference of the received first and second output signals; and
   linearizing means for determining the relative concentration of said two substances based on the determined ratio and the determined phase difference.

3. A device according to claim 1, wherein said transmitter transmits an S-band frequency signal through said mixture of said two substances.

4. A device according to claim 3, wherein said S-band frequency signal has a frequency of 2.45 GHz.

5. A device according to claim 2, wherein said transmitter transmits an S-band frequency signal through said mixture of said two substances.

6. A device according to claim 5, wherein said S-band frequency signal has a frequency of 2.45 GHz.

7. A device according to claim 1, wherein said first receiving element is twice as far away from said transmitter as is said second receiving element.

8. A device according to claim 2, wherein said first receiving element is twice as far away from said transmitter as is said second receiving element.

9. A device according to claim 3, wherein said first receiving element is twice as far away from said transmitter as is said second receiving element.

10. A device according to claim 4, wherein said first receiving element is twice as far away from said transmitter as is said second receiving element.

11. A device according to claim 5, wherein said first receiving element is twice as far away from said transmitter as is said second receiving element.

12. A device according to claim 6, wherein said first receiving element is twice as far away from said transmitter as is said second receiving element.

13. A device according to claim 2, wherein said linearizing means comprises:
   a look-up table.

14. A device according to claim 5, wherein said linearizing means comprises:
   a look-up table.

15. A device according to claim 8, wherein said linearizing means comprises:
   a look-up table.

* * * * *

UNITED STATES PATENT AND TRADEMARK OFFICE
CERTIFICATE OF CORRECTION

PATENT NO. : 5,101,163
DATED : March 31, 1992
INVENTOR(S) : Joram Agar

It is certified that error appears in the above-identified patent and that said Letters Patent is hereby corrected as shown below:

On the title page, in item (73):
The assignee is incomplete, should be, --Agar Corporation Ltd., Grand Cayman, Cayman Islands--, and the inventor is incomplete, should be, --Joram Agar, Grand Cayman, Cayman Islands--.

Signed and Sealed this

Sixth Day of July, 1993

Attest:

MICHAEL K. KIRK

Attesting Officer

Acting Commissioner of Patents and Trademarks

EX PARTE REEXAMINATION CERTIFICATE (4992nd)

United States Patent
Agar

(10) Number: US 5,101,163 C1
(45) Certificate Issued: Sep. 21, 2004

(54) OIL/WATER MEASUREMENT

(75) Inventor: Joram Agar, Grand Cayman (KY)

(73) Assignee: Agar Corporation Ltd., Grand Cayman (KY)

Reexamination Request:
No. 90/005,032, Jul. 2, 1998

Reexamination Certificate for:
Patent No.: 5,101,163
Issued: Mar. 31, 1992
Appl. No.: 07/675,061
Filed: Mar. 26, 1991

Certificate of Correction issued Jul. 6, 1993.

Related U.S. Application Data

(63) Continuation of application No. 07/417,658, filed on Oct. 4, 1989, now abandoned.

(51) Int. Cl.$^7$ .............................................. G01N 22/04
(52) U.S. Cl. ........................ 324/639; 324/640; 324/647; 324/698
(58) Field of Search ................................ 324/637, 639, 324/640, 641, 642, 643, 647, 698; 73/61.41, 61.43, 61.44, 61.61

(56) References Cited

U.S. PATENT DOCUMENTS 4,862,060 A * 8/1989 Scott et al. .................. 324/639
4,996,489 A * 2/1991 Sinclair ...................... 324/639

FOREIGN PATENT DOCUMENTS

| JP | 58-65526 | * | 5/1983 |
| JP | 59-19814 | * | 2/1984 |
| JP | 59-75137 | * | 4/1984 |
| JP | 62238444 | * | 10/1987 |

* cited by examiner

Primary Examiner—Glenn Brown

(57) ABSTRACT

A device for measuring the concentration of two substances through the transmission of electromagnetic waves. The device utilizes at least one transmission element for transmitting a signal and at least two receiving elements for receiving a signal from the at least one transmission element and providing first and second output signals. The present invention also utilizes a receiving device for receiving the first and second output signals from the at least two receiving elements such that the difference or ratio of the two signals is utilized to determine the concentration.

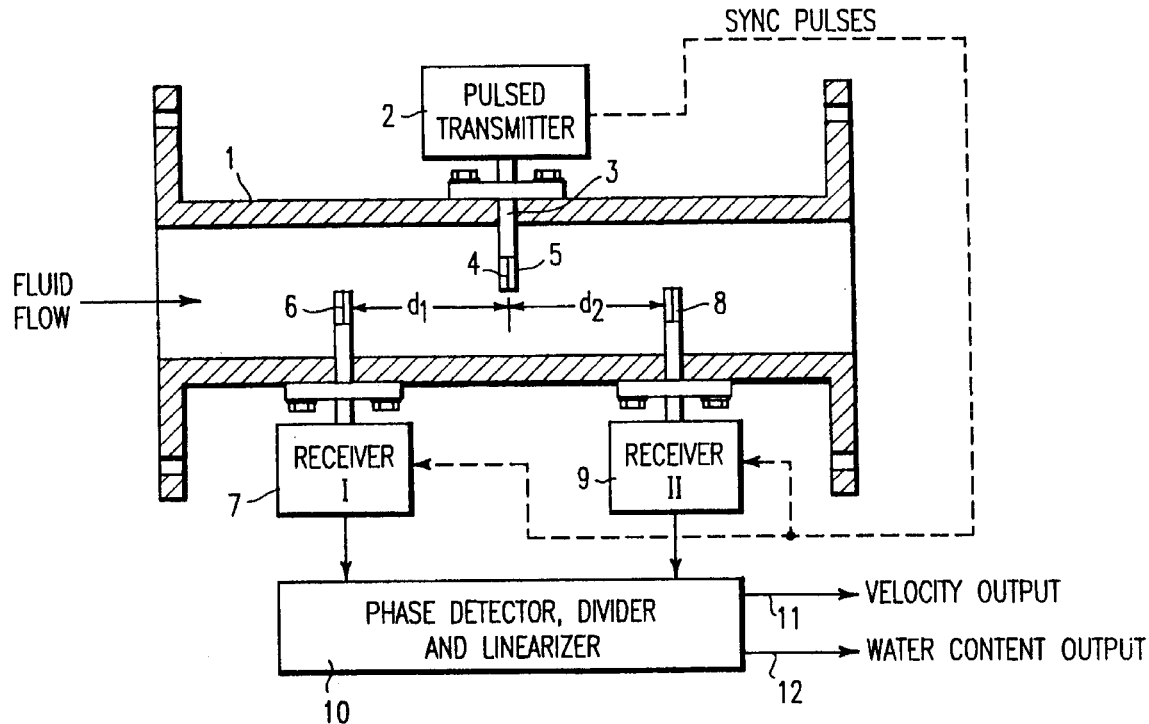

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

ONLY THOSE PARAGRAPHS OF THE SPECIFICATION AFFECTED BY AMENDMENT ARE PRINTED HEREIN.

Column 3, lines 3–15:

FIG. 2B shows an end view of FIG. 2A where one monopole transmitter antenna (4) is used in the center and two receiving antennae (13) and (14). FIG. 2B shows a circular cross-section waveguide, while FIG. 2C shows a similar arrangement with a rectangular cross-section waveguide. *As shown in FIGS. 2B, 2C and 3 by the double arrowed lines labeled "$d_1$" and "$d_2$", there are straight paths along which a signal transmitted by transmitter 4 may travel to the receiving elements 13 and 14, without being reflected. Thus, as shown in FIGS. 2B, 2C and 3, the first and second receiving elements 13 and 14 receive nonreflected signals transmitted along paths "$d_1$" and "$d_2$" from transmitter 4. The configurations shown in FIGS. 2B, 2C and 3 differ from a configuration where the same element functions as a transmitter and a receiver for the purpose of receiving a transmitted signal that is reflected back to the transmitter/receiver, such as a radar unit which measures doppler shift in order to calculate the speed of a motor vehicle.* Again, other types of conventional antennae can be used in this configuration such as two pairs of monopoles, "horn" type, etc. The transmitting antenna can be shared, or split into two separate ones. The advantage of two separate pairs is the elimination of cross-coupling between one receiving antenna and the other. The peripheral equipment surrounding the prime sensor is the same as shown in FIG. 1.

AS A RESULT OF REEXAMINATION, IT HAS BEEN DETERMINED THAT:

The patentability of claim 3 is confirmed.

Claims 1–3 are determined to be patentable as amended.

Claims 4–15, dependent on an amended claim, are determined to be patentable.

1. A device for measuring the concentration of two substances by means of the transmission of [electromagentic] *electromagnetic* waves through a mixture of said two substances, said device comprising:

a transmitter for transmitting through said mixture of said two substances a *nonreflected* signal within a predetermined frequency band;

first and second receiving elements for receiving the *nonreflected* signal transmitted by said transmitter through said mixture of said two substances and providing respective first and second output signals, said receiving elements being placed at two different distances from said transmitter; and, means for processing the first and second output signals to determine the concentration of the two substances using only the first and second output signals as variables obtained by means of *nonreflected* transmission and reception of *the nonreflected* signal[s] through said mixture of said two substances.

2. A device [according to claim 1,] *for measuring the concentration of two substances by means of the transmission of electromagnetic waves through a mixture of said two substances, said device comprising:*

*a transmitter for transmitting through said mixture of said two substances a signal within a predetermined frequency band;*

*first and second receiving elements for receiving the signal transmitted by said transmitter through said mixture of said two substances and providing respective first and second output signals, said receiving elements being placed at two different distances from said transmitter; and,*

*means for processing the first and second output signals to determine the concentration of the two substances using only the first and second output signals as variables obtained by means of transmission and reception of signals through said mixture of said two substances* wherein said processor means comprises[:]

means for determining the ratio of the powers of the received first and second output signals;

means for determining a phase difference of the received first and second output signals; and linearizing means for determining the relative concentration of said two substances based on the determined ratio and the determined phase difference.

\* \* \* \* \*